(12) United States Patent
Fatiny

(10) Patent No.: US 9,192,452 B2
(45) Date of Patent: Nov. 24, 2015

(54) PLASTIC CLEAR BAND FOR DENTAL RESTORATIONS

(75) Inventor: Fahad Ibrahim Fatiny, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 13/218,413

(22) Filed: Aug. 25, 2011

(65) Prior Publication Data

US 2013/0052608 A1 Feb. 28, 2013

(51) Int. Cl.
*A61C 5/12* (2006.01)

(52) U.S. Cl.
CPC ...................................... *A61C 5/125* (2013.01)

(58) Field of Classification Search
CPC ........... A61C 5/125; A61C 5/127; A61C 5/12
USPC ................. 433/37, 39, 40, 47, 155, 226, 229; D24/107, 156, 176, 181
See application file for complete search history.

(56) References Cited

U.S. PATENT DOCUMENTS

| | | | |
|---|---|---|---|
| 1,990,889 A | 2/1935 | Bandman | |
| 2,090,904 A | 8/1937 | Singer | |
| 2,439,703 A | 4/1948 | Tofflemire | |
| 2,594,367 A | 4/1952 | Tofflemire | |
| 3,020,638 A * | 2/1962 | Tofflemire | 433/155 |
| 3,108,377 A * | 10/1963 | Meyer | 433/39 |
| 3,795,052 A | 3/1974 | Mowery | |
| 4,778,385 A | 10/1988 | Herrin | |
| 5,248,258 A * | 9/1993 | Feldman | 433/39 |
| 5,330,353 A | 7/1994 | Wavrin | |
| 5,460,525 A | 10/1995 | Rashid | |
| 5,501,595 A * | 3/1996 | Brorson | 433/39 |
| 5,586,883 A * | 12/1996 | Nakisher et al. | 433/39 |
| 5,620,322 A | 4/1997 | Lococo | |
| 6,619,956 B1 | 9/2003 | Weir | |
| 6,749,429 B1 | 6/2004 | Haraden et al. | |
| 7,214,058 B2 | 5/2007 | Summer | |
| 7,367,802 B2 | 5/2008 | Viscomi et al. | |
| 2006/0019217 A1* | 1/2006 | Yates | 433/155 |
| 2007/0148613 A1* | 6/2007 | Stoll | 433/39 |
| 2007/0154860 A1 | 7/2007 | Kerle | |
| 2009/0142725 A1* | 6/2009 | Bryant et al. | 433/39 |
| 2009/0176192 A1* | 7/2009 | Vallittu et al. | 433/215 |
| 2011/0070555 A1 | 3/2011 | Anderson et al. | |

FOREIGN PATENT DOCUMENTS

JP 2000-60871 2/2000

OTHER PUBLICATIONS

Blue View™ Matrix Tape, Garrison Dental solutions website (www.garrisondental.com/store/blueview-matrix-tape/blue-view-matrix-tape.cfm).

* cited by examiner

*Primary Examiner* — Ralph Lewis
(74) *Attorney, Agent, or Firm* — Richard C. Litman

(57) ABSTRACT

The plastic clear band for dental restoration is a dental matrix band having an elongate body with first and second ends and at least one light transmissive portion midway between the first and second ends. The first and second ends have a thickness greater than the light transmissive portion, the band tapering in thickness from a thin central portion to the thick first and second ends. The thick first and second ends are adapted to provide a bearing surface for the clamping screws of a matrix band retainer, while the thin central portion provides a snug fit and tight contact with the tooth. The band is made from biocompatible plastic, and has an inverted V-shape or chevron configuration when viewed from the front.

14 Claims, 2 Drawing Sheets

PLASTIC CLEAR BAND FOR DENTAL RESTORATIONS

BACKGROUND OF THE INVENTION

1. Field of the Invention

The present invention relates dental implements, and particularly to a plastic clear band for dental restorations that provides a matrix band that can be used with a TOFFLEMIRE Universal retainer to provide a temporary mold when repairing the crown of a tooth or other dental restorations.

2. Description of the Related Art

The TOFFLEMIRE matrix system, developed by Dr. Joseph Tofflemire, includes a matrix band that is formed into a loop around a tooth and held in place by a clamp referred to as a TOFFLEMIRE Universal retainer to provide a temporary mold that the dentist fills with an amalgam, composite, or other matrix material when repairing the tooth. The band is used to temporarily replace missing parts of a prepared tooth and to confine restorative material to an area or areas prepared to receive the restorative material. The matrix band in the TOFFLEMIRE matrix system is typically made from a metal, such as stainless steel, and generally forms a funnel shape when formed into a loop in order to conform to the small diameter gingival surfaces and larger diameter occlusal surfaces of the tooth.

Currently, celluloid or similar light transmissive polymeric band materials are being used in place of metal, especially in the situations where it is desired to use polymeric materials, such as UV-hardening resins, for reconstructive purposes. However, this type of band is, by its very nature, uniformly thin along its entire length, flexible, and tends to be smooth and therefore somewhat slippery and difficult to manipulate. Such polymeric bands are difficult to position in TOFFLEMIRE Universal retainers and other similar matrix retainers, and also may slip during band tightening, for example. Because of these problems, TOFFLEMIRE Universal retainers and other similar matrix band retainers and clamps continue to use only metal matrix bands. Thus, a plastic clear band for dental restorations solving the aforementioned problems is desired.

SUMMARY OF THE INVENTION

The plastic clear band for dental restoration is a dental matrix band having an elongate body with first and second ends and at least one light transmissive portion midway between the first and second ends. The first and second ends have a thickness greater than the light transmissive portion, the band tapering in thickness from a thin central portion to the thick first and second ends. The thick first and second ends are adapted to provide a bearing surface for the clamping screws of a matrix band retainer, while the thin central portion provides a snug fit and tight contact with the tooth. The band is made from biocompatible plastic, and has an inverted V-shape or chevron configuration when viewed from the front.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
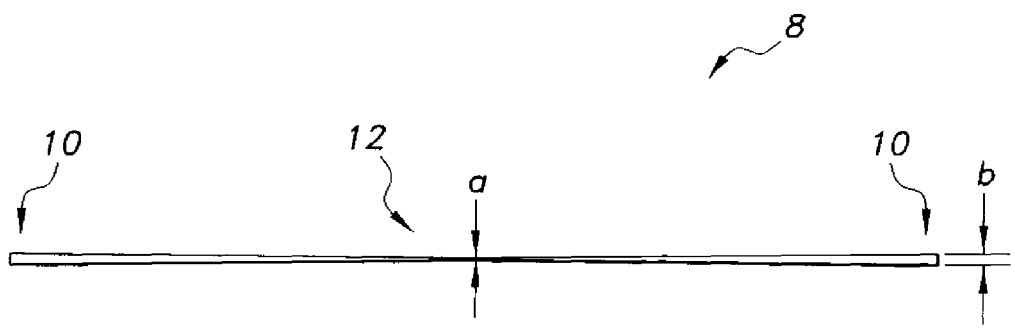
FIG. 1 is a top view of a plastic clear band for dental restorations according to the present invention.
Figure 2:
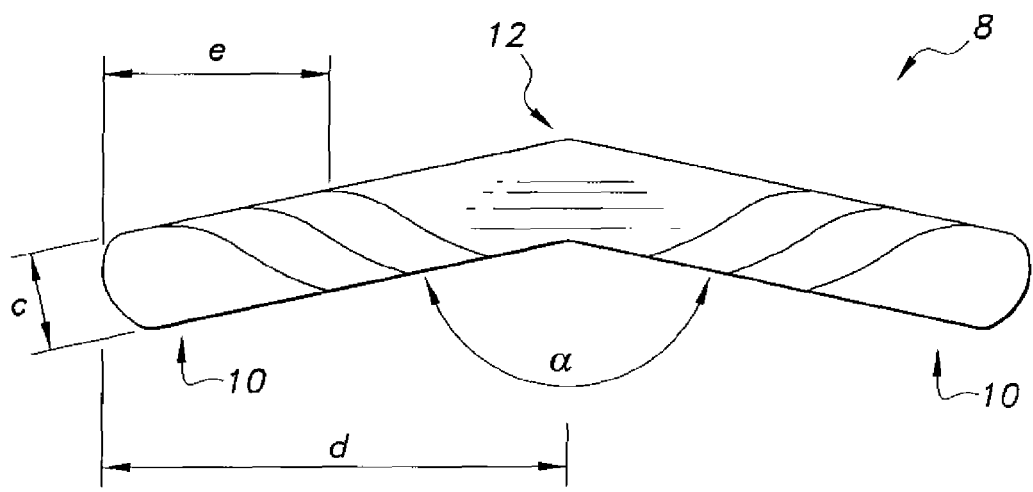
FIG. 2 is a front view of the plastic clear band of FIG. 1.
Figure 3:
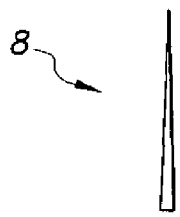
FIG. 3 is an end view of the plastic clear band of FIGS. 1 and 2.

The plastic clear band for dental restorations is depicted in FIGS. 1-3. As will be appreciated, the band 8 is chevron or boomerang-shaped, having first and second ends 10 and a central mid-portion 12 defined therebetween. The central mid-portion 12 is substantially translucent, while the end portions 10 can be less translucent and/or opaque. The end portions 10 can be colored as desired. The chevron-shaped band defines an angle $\alpha$ of about 135°.

The thickness of the band progressively increases towards the end portions to a maximum dimension b of about 0.05", by way of example, thus producing a wedge-like configuration. The mid or center portion, on the other hand, is sufficiently thin (dimension a is about 0.0005", for example) that it provides the desired flexibility while maintaining sufficient strength to permit safe and ready disposition about a tooth during dental restorations, as such shown in FIG. 5.

The band 8 preferably has a width c of about 7 mm, a half-length d of about 32 mm, thicker colored or opaque segments e towards the ends 10 of about 12 mm. It will be appreciated that these dimensions are merely exemplary and provided for purposes of enablement, and not for limitation. The above length and thickness dimensions can be varied, along with the angular measure of $\alpha$, as required.

The translucency of the central mid-portion 12 allows for the use of composite dental repair materials that harden in response to ultraviolet or other types of light. Merely by way of example, the central mid-portion 12 can be a clear, translucent yellow in color, while the thicker end portions 10 can be an opaque blue or the like.

Figure 4:
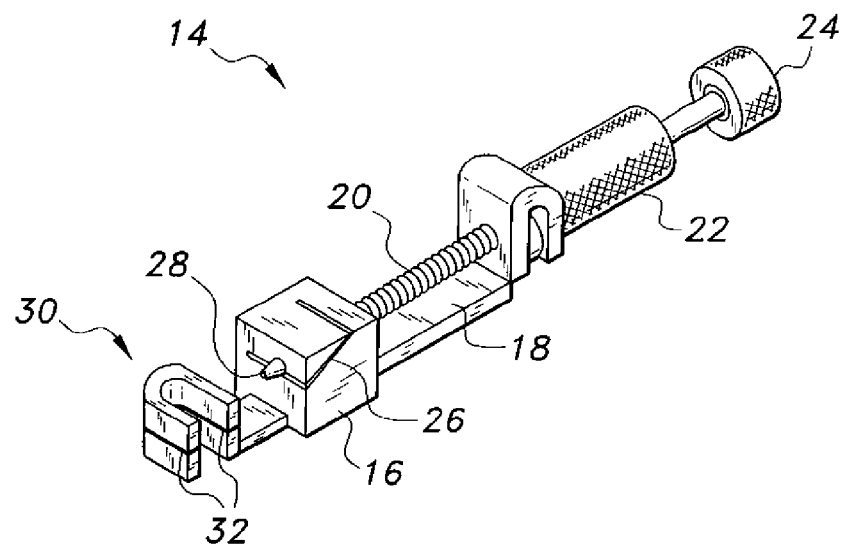
FIG. 4 is a perspective view of a TOFFLEMIRE Universal matrix retainer.

The band 8 is used in connection with a TOFFLEMIRE Universal retainer 14, shown in FIG. 4. The retainer 14 has a connection block 16 slidably disposed on a rail member 18. The connection block 18 is operatively connected with a threaded shaft 20 so that rotation of the inner and outer nuts 22, 24 can move the connection block 16 along the rail member 18 and then secure it in place. The connection block 16 is formed with a slot 26 to receive the wedge-like ends 10 of the band 8, and is provided with a pin 28 that stabilizes the band 8 when the ends 10 are disposed in the slot 26.

Figure 5:
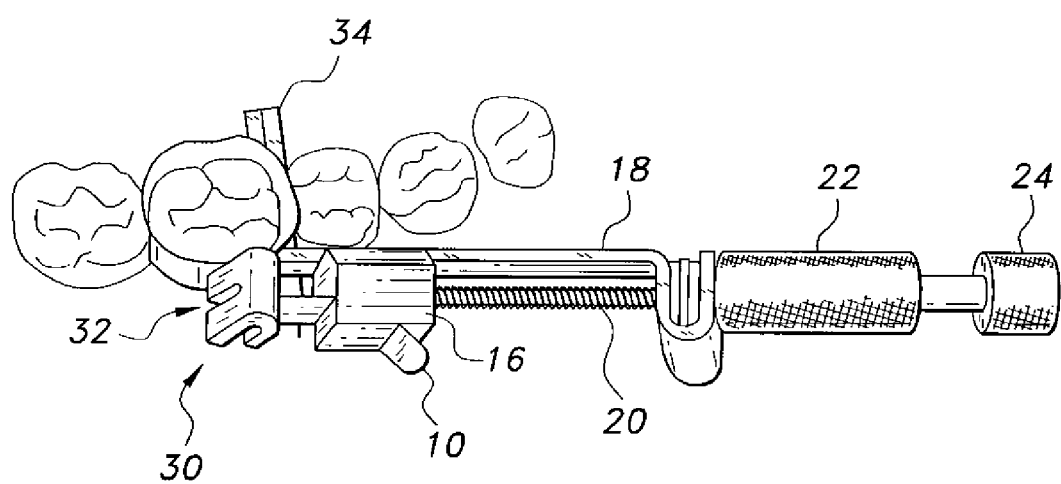
FIG. 5 is an environmental perspective view of a plastic clear band for dental restorations according to the present invention.

The end of the rail 18 is provided with a U-shaped member 30, which is provided with slots 32 and is arranged to appropriately hold the band 8 in position in the manner depicted in FIG. 5. A wedge 34 is illustrated in FIG. 5, showing its disposition holding the band 8 in position once appropriately located and tightened about a tooth requiring dental work/restoration.

As shown in FIG. 5, the wedge-like ends 10 of the band project out of the slot 26 due to their increasing thickness, which produces an effect that tends to "wedge" them in a slip free position and provide a bearing surface for a clamping screw securing the band to the retainer 14.

For further disclosure relating to this type of device, reference can be had to U.S. Pat. No. 2,439,703 published on Apr. 13, 1948 in the name of B.F. Tofflemire, and to U.S. Pat. No.

5,460,525 issued on Oct. 24, 1995 in the name of Rashid. The contents of these patents are hereby incorporated by reference in their entirety.

When used with the above-described retainer 14, the effect of the thickened ends 10 is such as to double the thickness of the portion of the ends of the band 8 which are received in the slot 26 of the connection block 16. That is to say, when the band 8 is used with the retainer 14, the ends 10 are placed together to form a loop of the band 8, and then, after being threaded into position via slots 32, the ends 10 are disposed in the slot 26 of the connection block 16 in the manner depicted in FIG. 5. This provides a thickness that is markedly greater than that possible with bands having uniform thickness, and enables a snug, and slip-free wedging type connection with the connection block 16, and thus facilitates the band tightening procedure associated with the dental procedure in hand.

The bands can be formed, e.g., by extruding a sheet or strip of material having a cross-section of the nature illustrated in FIG. 1 and cutting the strip into the bands having the configuration depicted in FIG. 2.

It is to be understood that the present invention is not limited to the embodiments described above, but encompasses any and all embodiments within the scope of the following claims.

I claim:

1. A plastic clear band for dental restorations, consisting of a band made of plastic material, wherein the band is a strip having a chevron configuration defining an angle of approximately 135°, the band further defining an elongate body having first and second longitudinally-opposed ends, a front, a back, and a central light transmissive portion disposed midway between the first and second longitudinally-opposed ends, the first and second longitudinally-opposed ends having a transverse thickness greater than the central light transmissive portion, the band tapering in transverse thickness from the thick first and second ends to the thin central portion thereby defining respective first and second V-shaped wedge configurations, wherein each of the first and second longitudinally-opposed ends is rounded, the band having segments extending towards the first and second longitudinally-opposed ends, at least one of the segments tapering in transverse thickness from the front towards the back thereby defining a third V-shaped wedge configuration having the apex of the third V-shaped wedge configuration at the front, a longitudinal length between the first and second longitudinally-opposed ends being approximately 64 mm, a transverse thickness of each of the first and second ends being approximately 0.05 inches, and a transverse thickness of the central light transmissive portion being approximately 0.0005 inches, the band being bendable to form a loop adapted for surrounding a tooth, the thickness of the first and second ends being adapted to provide secure retention in a slot of a matrix retainer used to clamp the looped band to the tooth during a dental restoration procedure.

2. The plastic clear band for dental restorations according to claim 1, wherein the first and second ends are colored differently from the light transmissive portion.

3. The plastic clear band for dental restorations according to claim 1, wherein the first and second ends are opaque.

4. The plastic clear band for dental restorations according to claim 1, wherein each of the first and second longitudinally-opposed ends has a width of approximately 7 mm.

5. A dental matrix kit, comprising:
a slotted matrix retainer; and
a matrix band made of plastic material, wherein the band consists of a strip having a chevron configuration defining an angle of approximately 135°, the band further defining an elongate body having first and second longitudinally-opposed ends, a top, a bottom, and a central light transmissive portion disposed midway between the first and second longitudinally-opposed ends, the first and second longitudinally-opposed ends having a transverse thickness greater than the central light transmissive portion, the band tapering in transverse thickness from the thick first and second ends to the thin central portion thereby defining respective first and second V-shaped wedge configurations, wherein each of the first and second longitudinally-opposed ends is rounded, the band having segments extending towards the first and second longitudinally-opposed ends, at least one of the segments tapering in transverse thickness from the top towards the bottom thereby defining a third V-shaped wedge configuration having the apex of the third V-shaped wedge configuration at the top, a longitudinal length between the first and second longitudinally-opposed ends being approximately 64 mm, a transverse thickness of each of the first and second ends being approximately 0.05 inches, and a transverse thickness of the central light transmissive portion being approximately 0.0005 inches, the band being bendable to form a loop adapted for surrounding a tooth, the thickness of the first and second ends being adapted to provide secure retention in the slotted matrix retainer used to clamp the looped band to the tooth during a dental restoration procedure.

6. A plastic clear band for dental restorations comprising a band made of plastic material, wherein the band is a strip having a chevron configuration defining an obtuse angle, the band further defining an elongate body having first and second longitudinally-opposed ends, a top, a bottom, and a central light transmissive portion disposed midway between the first and second longitudinally-opposed ends, the first and second longitudinally-opposed ends having a transverse thickness greater than the central light transmissive portion, the band tapering in transverse thickness from the thick first and second ends to the thin central portion thereby defining respective first and second V-shaped wedge configurations, the band having segments extending towards the first and second longitudinally-opposed ends, at least one of the segments tapering in transverse thickness from the top towards the bottom thereby defining a third V-shaped wedge configuration having the apex of the third V-shaped wedge configuration at the top, the band being bendable to form a loop adapted for surrounding a tooth, the thickness of the first and second ends being adapted to provide secure retention in a slot of a matrix retainer used to clamp the looped band to the tooth during a dental restoration procedure.

7. The plastic clear band for dental restorations according to claim 6, wherein the obtuse angle is approximately 135°.

8. The plastic clear band for dental restorations according to claim 6, wherein each of the first and second longitudinally-opposed ends is rounded.

9. The plastic clear band for dental restorations according to claim 6, wherein a longitudinal length between the first and second longitudinally-opposed ends is approximately 64 mm.

10. The plastic clear band for dental restorations according to claim 6, wherein a transverse thickness of each of the first and second ends is approximately 0.05 inches.

11. The plastic clear band for dental restorations according to claim 6, wherein a transverse thickness of the central light transmissive portion is approximately 0.0005 inches.

12. The plastic clear band for dental restorations according to claim 6, wherein the first and second ends are colored differently from the light transmissive portion.

13. The plastic clear band for dental restorations according to claim 6, wherein the first and second ends are opaque.

14. The plastic clear band for dental restorations according to claim 6, wherein each of the first and second longitudinally-opposed ends has a width of approximately 7 mm.

* * * * *